US005483836A

United States Patent [19]
Kinnebrew

[11] Patent Number: 5,483,836
[45] Date of Patent: Jan. 16, 1996

[54] DEVICE FOR MEASURING LATERAL DEFORMATIONS IN MATERIAL TEST SPECIMENS

[75] Inventor: Stephen Kinnebrew, Vicksburg, Miss.

[73] Assignee: U.S. Army Corps of Engineers as represented by the Secretary of the Army, Washington, D.C.

[21] Appl. No.: 215,745

[22] Filed: Mar. 21, 1994

[51] Int. Cl.⁶ .................................................. G01N 3/00
[52] U.S. Cl. ................................................ 73/795; 73/794
[58] Field of Search ............................ 73/783, 795, 794, 73/812, 831, 833, 849, 855, 856

[56] References Cited

U.S. PATENT DOCUMENTS

| | | | |
|---|---|---|---|
| 2,866,333 | 4/1965 | Dudenhausen | 73/862.042 |
| 3,433,060 | 7/1966 | Ives et al. | 73/812 |
| 4,866,992 | 9/1989 | Rice et al. | 73/831 |
| 4,875,375 | 10/1989 | Wu et al. | 73/794 |
| 5,065,631 | 11/1991 | Ashpitel et al. | 73/849 |

Primary Examiner—Richard Chilcot
Assistant Examiner—Max Noori
Attorney, Agent, or Firm—Luther A. Marsh

[57] ABSTRACT

Disclosed is a device for measuring lateral deformation in an material specimen which includes a generally ring shaped frame member displaced generally perpendicularly to the object being measured. The frame member itself comprises a first and a second generally arc shaped element which abut end to end. At least one spring arm member is fixed at one end on a mounting projection on the first arc shaped element and its movable end abuts a spring receiving projection from the second generally arc shaped element. Strain gauges are fixed to the spring arm member to detect changes in the flexture of the spring arm member resulting from relative movement of the two arc shaped elements which results from lateral deformation of the material specimen. A linear variable differential transformer having a lateral projection is also mounted on one of the arc shaped elements. The lateral projection bears against a reaction arm mounted on the other of the arc shaped elements to measure small deformations which may not be sensed by the strain gauges on the spring arm members.

12 Claims, 3 Drawing Sheets

5,483,836

DEVICE FOR MEASURING LATERAL DEFORMATIONS IN MATERIAL TEST SPECIMENS

BACKGROUND OF THE INVENTION

1. Field of the Invention

The present invention relates to instruments for measuring and testing and, more particularly to, instruments for measuring deformation of materials.

2. Description of the Prior Art

In tri-axial compression tests lateral deformations in material test specimens are conventionally measured with either cantilevered spring arms which are equipped with electrical strain gauges or linear variable differential transformers. Both methods require that the deformeter be mounted on a "bird cage" surrounding the specimen. Lateral deformations may be difficult to measure by such means due to the fact that specimens deform not only laterally but longitudinally. It may also be difficult to account for the compressibility of the membrane which is conventionally used to surround the specimen using such methods. A disadvantage which is particularly applicable to the use of linear variable differential transformers is that they have limited range and are easily damaged during uncontrolled specimen failure.

Strain path tests in which strain gauges are adhered directly to the specimen are also conventionally used to measure lateral deformations. Such direct attachment is required due to the necessity that deformeters used in such tests have infinite resolution. Direct attachment in this manner requires that the sides of the specimen be very smooth and free of voids. Because of the requirement of such smoothness many rock and concrete materials can not be tested by this method.

SUMMARY OF THE INVENTION

It is an object of the present invention to provide a device for accurately measuring the lateral response of material specimens undergoing various states of stress and strain during tests to determine their mechanical properties which avoids the disadvantages of the above described prior art deformeters. In particular, it is an object of the present invention to provide a device which is capable of measuring large lateral deformations up to about 500 mils while also having the capability of sensing very small lateral responses of less than about 0.002 mils based on a specimen having an original diameter of 2 inches.

It is a further object of the present invention to provide a device for measuring lateral deformations which accurately measures the lateral response of materials requiring the use of multiple membranes and which also requires no membrane compressibility correction.

It is a further object of the present invention to provide a device for measuring lateral deformations which is capable of strain path tests measuring small lateral deformations on specimens on which strain gauges can not be affixed to the surfaces.

It is a further object of the present invention to provide a device for measuring lateral deformations which allows the center of a specimen to be constantly tracked while the specimen is being deformed vertically.

It is a further object of the present invention to provide a device for measuring lateral deformations which has the ability to survive in uncontrolled specimen failure.

In the device of the present invention there is generally ring shaped frame member positioned perpendicularly to the longitudinal axis of the specimen being measured. This frame member itself comprises a first and a second generally arc shaped element which abut and are preferably pivotally connected at their terminal ends. Adjacent the terminal ends of the first arc shaped members there is a spring mounting means and in a generally corresponding position on the second arc shaped element there is a spring receiving means. Spring arm members are retained at their fixed ends on the spring mounting means and extend therefrom to abut the spring receiving means adjacent their movable ends. At least one strain measuring means is fixed to the spring arm member to detect changes in the flexure of the spring arm member between the spring mounting means and the spring receiving means due to relative movement of the two arc shaped elements resulting from lateral deformation of the specimen.

A linear variable differential transformer having a lateral projection is also preferably mounted on one of the arc shaped elements. The lateral projection bears against a reaction arm mounted on the other of the arc shaped elements to measure small deformations which may not be sensed by the strain gauges on the spring arm members.

The device is advantageously used to measure lateral deformations in cylindrical concrete and rock specimens. It may, however, also be used to measure specimens of other shapes and materials.

BRIEF DESCRIPTION OF THE DRAWINGS

The device of the present invention is further described with reference to the accompanying drawings in which.

DESCRIPTION OF THE PREFERRED EMBODIMENT

Figure 3:
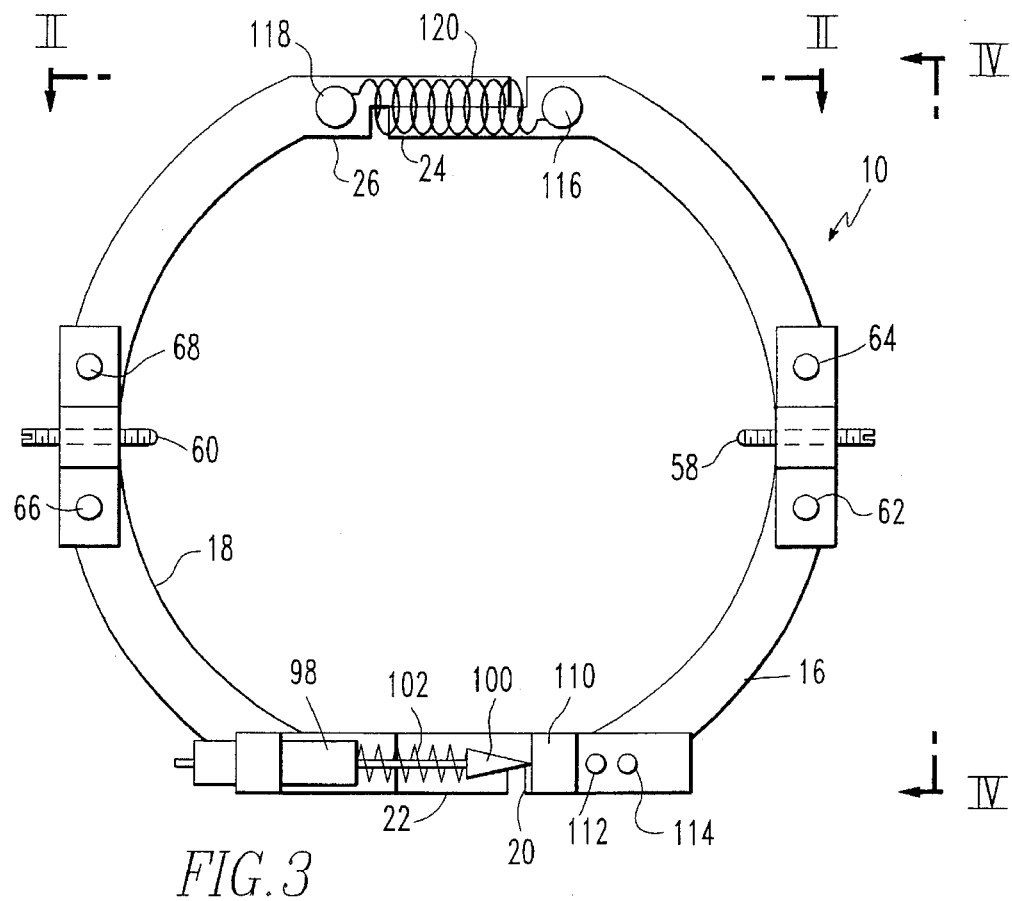
FIG. 3 is a plan view of the device for measuring lateral deformations shown in FIG. 1.

Referring to FIGS. 1–5, it will be seen that the device for measuring lateral deformation includes a generally ring shaped frame member shown generally at numeral 10. This frame mender is disposed generally perpendicularly to the specimen 12 (FIG. 5) being measured. For the purposes of this disclosure, the vertical axis 14 of the specimen shown in FIG. 5 will be considered to be its "longitudinal" axis and directions perpendicular to this axis will be considered to be "lateral", and these terms will be used in the same manner herein to describe the position of the elements of the device as well as the specimen to be measured. It will also be seen that the frame itself is comprised of a first arc shaped element 16 and a second arc: shaped element 18. The first arc shaped element and the second arc shaped element both have adjoining first terminal ends respectively at 20 and 22 and adjoining second terminal ends respectively at 24 and 26. These first terminal ends are pivotally connected by pin 28, and the second terminal ends are pivotally connected by pin 30.

Figure 1:
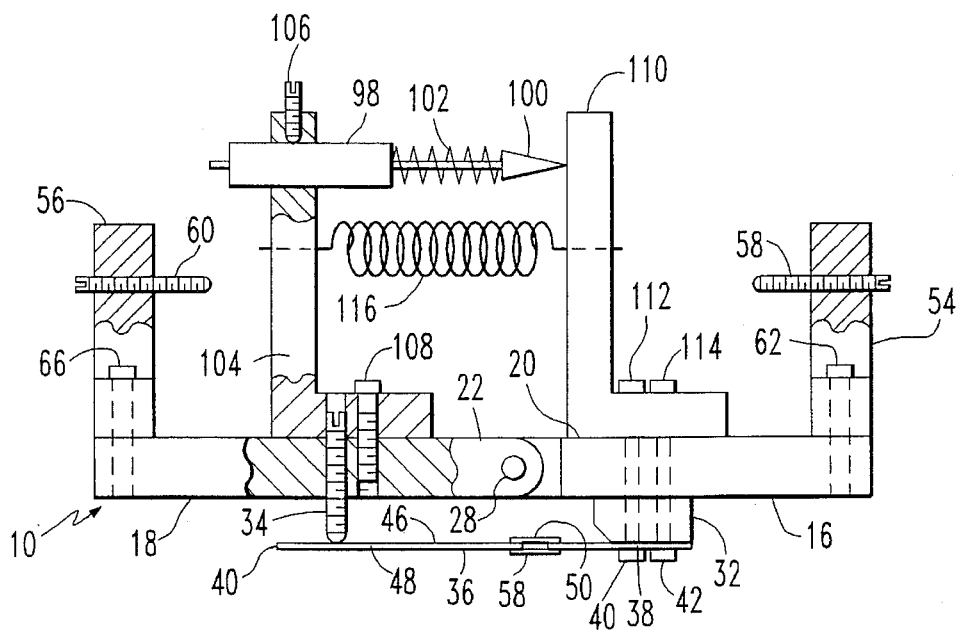
FIG. 1 is a front elevational view of a preferred embodiment of the device for measuring lateral deformations of the present invention.

Referring particularly to FIG. 1, it will be seen that there is a longitudinally downward projection 32 on the first arc shaped element adjacent the first terminal end which serves as a spring arm member mounting means. On the second arc shaped element adjacent its first terminal end there is another adjustable longitudinally downward projection 34 which serves as a spring receiving means. A spring arm member 36 having a fixed end 38 and a movable end 40 and being restrained at its fixed end on the spring mounting means by means of screws 42 and 44. The spring arm member 36 extends from the spring retaining projection to abut the spring receiving projection adjacent its movable end. There is at least one strain measuring means fixed to the spring arm member to detect changes in the flexure of the spring arm member between the spring mounting means and the spring receiving means. In the preferred embodiment, the spring arm member has a top side 46 and a bottom side 48 and an electrical resistance strain gauge 50 is mounted on the top side of the spring arm member and another electrical resistance strain gauge 52 is mounted on the bottom side of the spring arm member. It will be seen that this mounting arrangement allows the spring arm member to extend in spaced parallel relation to the frame member and to bear against the spring receiving projection so as to flex the spring arm member in response to movement of the first arc shaped element and the spring retaining projection relative to second arc shaped member and the spring receiving projection. As is explained in further detail below, the movement of the first arc shaped element relative to the second arc shaped element is in response to the lateral deformation of the specimen being tested.

In particular, this movement is pivotal motion resulting from the above described arrangement wherein the first arc shaped element is pivotally attached to the second arc shaped element at the first terminal ends of said first and second arc shaped elements so that the first arc shaped element is pivotable in a longitudinal arc relative to the second arc shaped element. It will be appreciated that the spring arm member flexes in response to the relative pivoting motion of the first arc shaped element to the second arc shaped element.

Referring particularly to FIGS. 1–5, it will be seen that a first specimen retaining post 54 is positioned medially between the first and second terminal ends of the first arc shaped element and a second opposed specimen retaining post 56 is positioned medially between the first and second terminal ends of the second arc shaped element. These specimen retaining posts project longitudinally upwardly from the frame member, and they both have specimen contact rods respectively at 58 and 60 which radially projecting toward each other in a lateral direction. Post 54 is fixed to the first arc shaped element of the frame by means of screws 62 and 64. Post 56 is fixed to the second arc shaped element of the frame by means of screws 66 and 68. The lengths of the specimen retaining rods are adjustable in length to engage the material specimen at various lateral distances from the specimen retaining posts and to accommodate various diameters of specimens. Those skilled in the art will appreciate that forces resulting from lateral deformations in a specimen will be transmitted through the contact rods and retaining posts to the frame to cause the first and second arc shaped elements to pivot with respect to each other and thus cause the spring arm member to flex.

Figure 5:
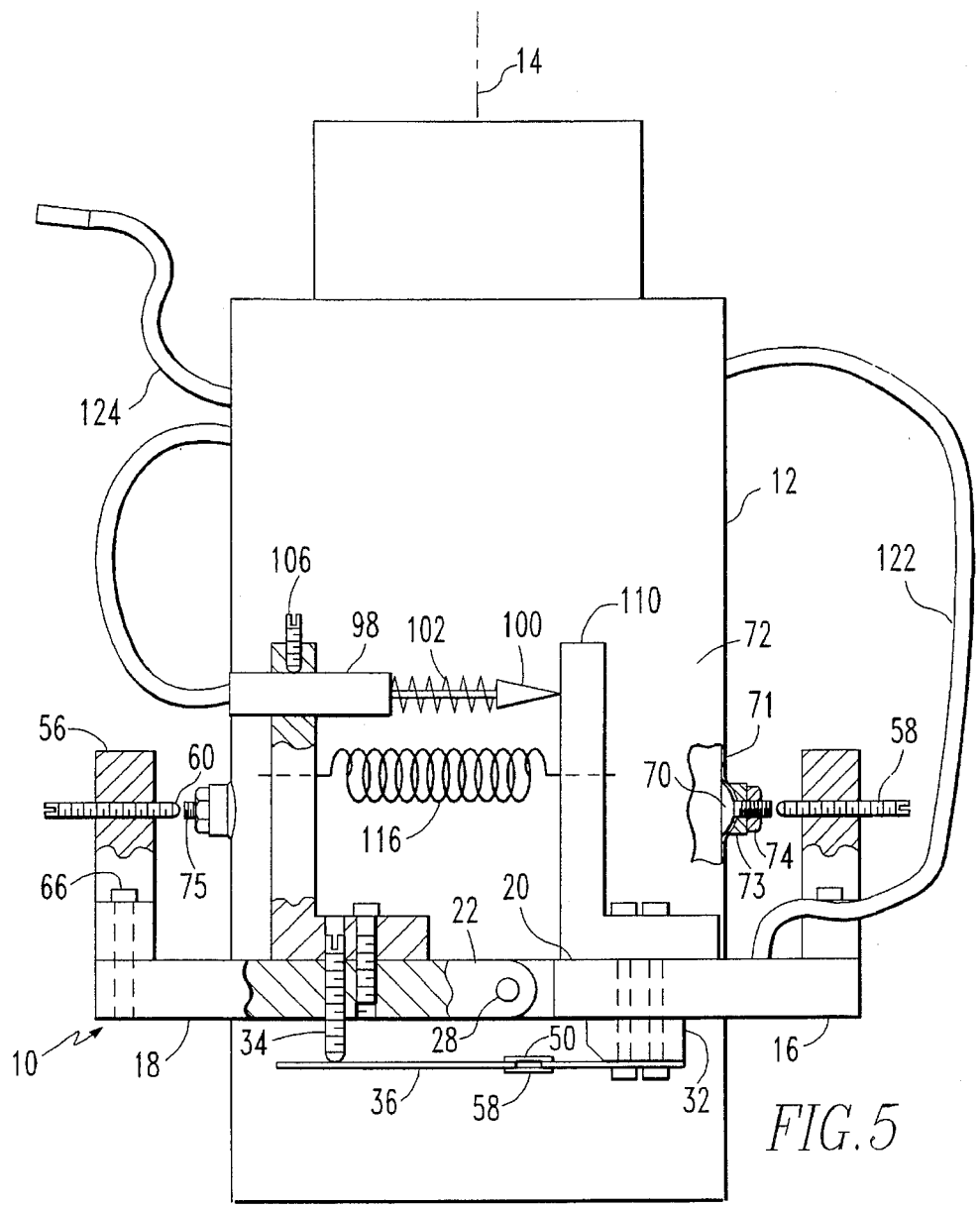
FIG. 5 is a front elevational view of the device for measuring lateral deformations shown in FIG. 1 in which the device is shown in conjunction with a specimen to be tested.
Figure 6:
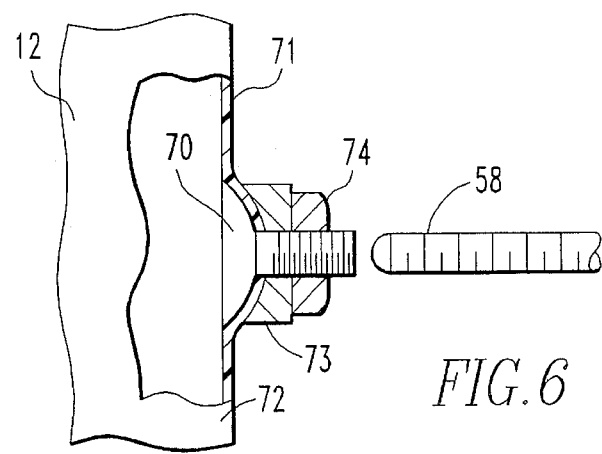
FIG. 6 is an enlarged cut away view showing the area surrounding member 70 in FIG. 5.

Referring particularly to FIGS. 5 and 6, it will be seen that the contact rods have at their terminal ends a specimen engaging footer as at 70 which have a concave specimen engaging surface and a central threaded lateral projection. This curve of the concave surface of this footer will preferably match or approximate the curve of the cylindrical specimen. The membrane 71 will be cut away in a small circular pattern to allow the footer to bear directly against the concrete or rock surface 74 of the specimen. A cupped washer 73 fits over the projecting section of the footer and a nut 74 engages the threads of that section. The contact rod 58 may be adjusted in length to bear against this footer. The contact rod 60 bears against another similar footer 75.

Figure 2:
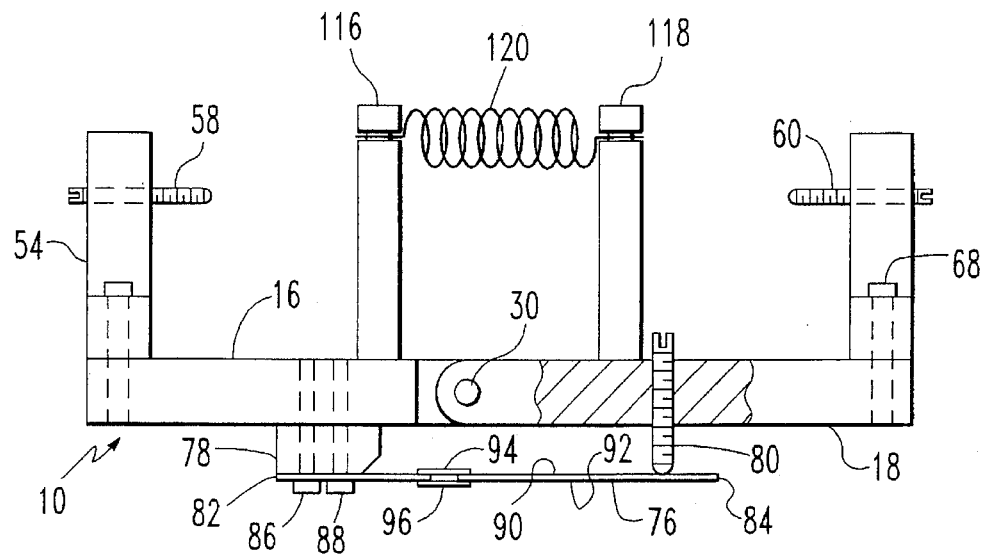
FIG. 2 is a rear view of the device for measuring lateral deformations shown in FIG. 1 from line II—II.

Referring particularly to FIG. 2, it will be seen that a second spring arm member 76 is positioned in a manner similar to the arrangement described above in connection with spring arm member 36. That is, there is a longitudinally downward projection 78 on the first arc shaped element adjacent the first terminal end which serves as a spring mounting means. On the second arc shaped element adjacent its first terminal end there is another adjustable longitudinally downward projection 80 which serves as a spring receiving means. The spring arm member 76 has a fixed end 82 and a movable end 84 and is restrained at its fixed end on the spring mounting means by means of screws 86 and 88. The spring arm member 76 extends from the spring retaining projection to abut the spring receiving projection adjacent its movable end. There is at least one strain measuring means fixed to the spring arm member to detect changes in the flexure of the spring arm member between the spring mounting means and the spring receiving means. In this preferred embodiment, the spring arc member has a top side 90 and a bottom side 92 and an electrical resistance strain gauge 94 is mounted on the top side of the spring arm member and another electrical resistance strain gauge 96 is mounted on the bottom side of the spring arm member. As with the mounting arrangement of spring arm member 36, this mounting arrangement allows the spring arm member 76 to extend in spaced parallel relation to the frame member and to bear against the spring receiving projection 80 so as to flex the spring arm member 76 in response to movement of the first arc shaped element and the spring retaining projection 78 relative to second arc shaped member and the spring receiving projection 80. As was explained above, the movement of the first arc shaped element relative to the second arc shaped element is in response to the lateral deformation of the specimen being tested.

Referring again particularly to FIGS. 1–5, it will be seen that the device includes a linear variable differential transformer (LVDT) 98 which has a lateral projection 100 equipped with a compression spring 102. A suitable LVDT is available from Schaevitz Engineering of Pennsauken, N.J. as Model 500 MHR. The LVDT is mounted on the second arc shaped element on a vertical mounting projection 104. The LVDT is retained on this mounting projection by means of screw 106 and the mounting projection is fixed to the second arc shaped element by means of screws as at 108. The lateral projection bears against a reaction arm 110 which is mounted on the first arc shaped element by means of screws 112 and 114. The compression spring presses the lateral projection of the linear differential transformer against the reaction arm and this force is augmented by a lateral tension spring 116 which connects the mounting projection and the reaction arm.

Figure 4:
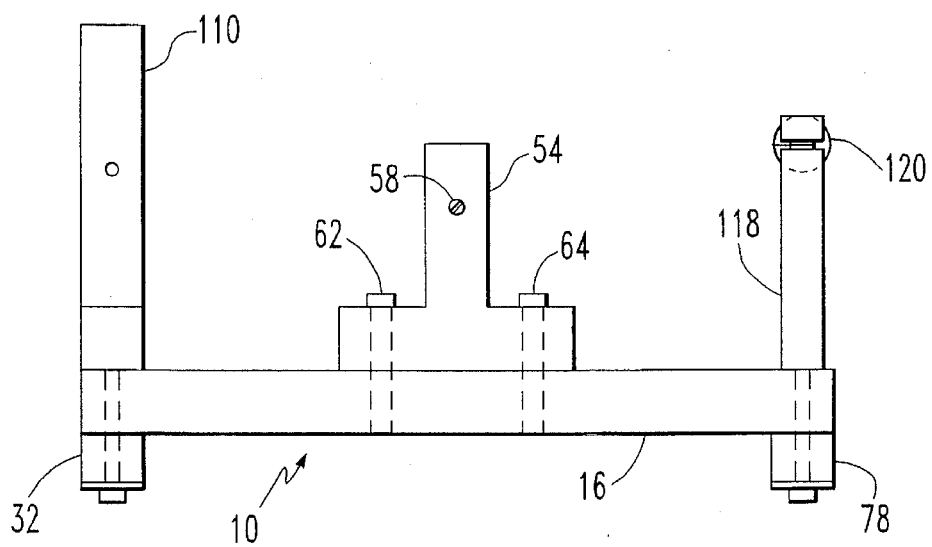
FIG. 4 is an end view of the device for measuring lateral deformations shown in FIG. 1 from line IV—IV.

Referring particularly to FIGS. 2–4, it will be seen that there is also a tension post 116 which projects longitudinally upwardly from the first arc shaped element adjacent its second terminal end. There is also another tension post 118 which projects longitudinally upwardly from the second arc shaped member adjacent its second terminal end. These tension posts are connected by a lateral tension spring 120.

Referring to FIG. 5, there is a cable 122 conducting current from the strain gauges and a cable 124 conducting current from the LVDT. Those skilled in the art will appreciate that these cables may be used to detect changes in voltages across the LVDT and the strain gauges which will be indicative of lateral deformation in the specimens. For example, the relative changes in resistance in the strain gauges on the upper side of spring arm members resulting from their compression may be compared with changes in resistance on the strain gauges on the lower side of the spring arm resulting from their tension side of the spring arm resulting from their tension may be monitored by means of a Wheatstone bridge where the two top resistors and the two bottom resistors are positioned on opposite sides of the device.

A preferred method of preparing a specimen for being tested with the above described device is to draw a vertical line along one side of the specimen. The specimen is then rotated 180 degrees and another vertical line is drawn. On each of these lines a mark is made at its midpoint. Using a strong adhesive such as EASTON 9/10, the footings are adhered to the sample at the midpoints marked in the previous step. A membrane is placed on the specimen and then a small hole is cut at the point where the membrane contacts the footing. Additional membranes may then be applied as needed using the same procedure. Next the cupped washer is placed onto the footings. The machine nut is then screwed onto the footing until contact is made with the washer while slightly compressing the membrane material between the washer and the base of the footing. The nut is not tightened too tightly as this action may cut the membrane or loosen the base of the footing form the specimen. Preferably the threaded end of the footing should be recessed approximately 25 mils below the outer edge of the nut.

The device is then set up as follows:

Using the sample containing posts as handles, the device is hinged open and positioned on the sample as shown in FIG. 5. The contact rods are to rest upon the footings with the nuts acting as guides to prevent the device from slipping off the footing. The contact rods are adjusted by screwing them in or out until the zero point setting is obtained.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A device for measuring lateral deformation in an material specimen having a longitudinal axis comprising:

(a) a generally ring shaped frame member displaced generally perpendicularly to the object being measured and itself comprising a first and a second generally arc shaped element each of said arc shaped elements having first and second terminal ends and being positioned so that the first terminal end of the first arc shaped member adjoins the first terminal end of the second arc shaped member and the second terminal end of the first arc shaped member adjoins the second terminal end of the second arc shaped member and the second terminal end of the first arc shaped member adjoins the second terminal end of the second arc shaped member and there being a spring mounting means on the first arc shaped element adjacent its first terminal end and a spring receiving means on the second arc shaped element adjacent its first terminal end; and wherein the spring mounting is a projection extending longitudinally from the first arc shaped element and the spring receiving means is a projection extending longitudinally from the second arc shaped element in the same direction as the spring mounting means such that the spring arm member extend in spaced parallel relation to the frame member and bears against the spring receiving means to flex the spring arm member in response to movement of the spring retaining means relative to the spring receiving means;

(b) a spring arm member having a fixed end and a movable end and being retained at its fixed end on the spring mounting means extending therefrom to abut the spring receiving means adjacent its movable end;

(c) at least one strain measuring means fixed to the spring arm member to detect changes in the flexture of the spring arm member between the spring mounting means and the spring receiving means, and wherein the spring arm member flexes in response to the lateral deformation of the object being measured; and (d) wherein the first arc shaped element is pivotally attached to the second arc shaped element at the first terminal ends of said first and second arc shaped elements so that the first arc shaped element is pivotable in a longitudinal arc relative to the second arc shaped elements.

2. The device of claim 1 wherein the first arc shaped element is pivotally attached to the second arc shaped element at the second terminal ends of said first and second arc shaped elements.

3. The device of claim 1 wherein the spring arm member flexes in response to the relative pivoting motion of the first arc shaped element to the second arc shaped element.

4. The device of claim 1 wherein the spring arm member has a top side and a bottom side and a strain measuring means is mounted on the top side of the spring arm member and another strain measuring means is mounted on the bottom side of the spring measuring means.

5. The device of claim 1 wherein a first specimen retaining post is positioned medially between the first and second terminal ends of the first arc shaped element and a second opposed specimen retaining post positioned is medially between the first and second terminal ends of the second arc shaped element project longitudinally from the frame member and said first specimen retaining post and second specimen retaining post both have specimen contact rods radially projecting toward each other.

6. The device of claim 5 wherein the first specimen retaining post and second specimen retaining post project from the frame member in an opposite direction from the spring retaining means and spring receiving means.

7. The device of claim 5 wherein the specimen contact rods are both adjustable in length to engage the material specimen at various lateral distances from the specimen retaining posts.

8. The device of claim 7 wherein the first arc shaped element is pivotally attached to the second arc shaped element at the first terminal ends of said first and second arc shaped elements and the first arc shaped element is pivotally attached to the second arc shaped element at the second terminal ends of said terminal ends of said first and second arc shaped elements so that the first arc shaped element is pivotable in a longitudinal arc relative to the second arc shaped element.

9. The device of claim 8 wherein the second spring arm member flexes in response to the relative pivoting motion of the first arc shaped element to the second arc shaped element.

10. The device of claim 9 wherein the second spring arm member has a top side and a bottom side and a strain measuring means is mounted on the top side of the spring arm member and another strain measuring means is mounted on the bottom side of the spring measuring means, 11. The device of claim 10 wherein a compression spring presses the lateral projection of the linear differential transformer against the reaction arm and a lateral tension spring connects said mounting means and the reaction arm.

12. The device of claim 11 wherein a tension post projects longitudinally from the first arc shaped member adjacent its second terminal end and another tension post projects longitudinally from the second arc shaped member adjacent its second terminal end and said tension post are connected by a lateral tension spring.

* * * * *